United States Patent
Sidewell et al.

(10) Patent No.: US 7,303,925 B2
(45) Date of Patent: Dec. 4, 2007

(54) METHOD OF DETECTING AN ANALYTE FOR LATERAL FLOW IMMUNOASSAY TESTS

(75) Inventors: Steven P. Sidewell, Dana Point, CA (US); Steven S. Bachand, Laguna Niguel, CA (US)

(73) Assignee: Varian Inc., Palo Alto, CA (US)

( * ) Notice: Subject to any disclaimer, the term of this patent is extended or adjusted under 35 U.S.C. 154(b) by 383 days.

(21) Appl. No.: 10/932,399

(22) Filed: Sep. 2, 2004

(65) Prior Publication Data

US 2005/0037519 A1    Feb. 17, 2005

Related U.S. Application Data

(62) Division of application No. 09/910,198, filed on Jul. 20, 2001, now Pat. No. 6,818,456.

(51) Int. Cl.
*G01N 33/53* (2006.01)
(52) U.S. Cl. ............ 436/518; 436/514; 436/161; 436/162; 436/810; 436/823; 422/55; 422/56; 422/58; 422/60
(58) Field of Classification Search ............. 436/518, 436/514, 810, 823, 161, 16; 422/55, 56, 422/58, 60
See application file for complete search history.

(56) References Cited

U.S. PATENT DOCUMENTS

| 4,303,409 A | * | 12/1981 | Ogawa et al. | 436/93 |
| 5,500,375 A | * | 3/1996 | Lee-Own et al. | 436/514 |
| 5,877,028 A | * | 3/1999 | Chandler et al. | 436/514 |
| 6,418,606 B1 | * | 7/2002 | Bachand | 29/412 |
| 6,833,111 B2 | * | 12/2004 | Robertson et al. | 422/58 |

OTHER PUBLICATIONS

Scientific Products General Catalog. p. 946. 1991.*

* cited by examiner

*Primary Examiner*—Bao-Thuy L. Nguyen
(74) *Attorney, Agent, or Firm*—Bella Fishman

(57) ABSTRACT

A visual perception of a colored site in an immunoassay device comprising a strip for enabling capillary migration of a fluid sample therealong, a labeled reagent disposed on the strip and formulated for suspension in the sample migrating therepast and a captive reagent immobilized on the strip in a path of sample migration and formulated to bind to is enhanced by changing a color of the strip to the color which is complimentary to the colored site.

5 Claims, 1 Drawing Sheet

METHOD OF DETECTING AN ANALYTE FOR LATERAL FLOW IMMUNOASSAY TESTS

CROSS-REFERENCE TO RELATED APPLICATION

This application is a divisional of application Ser. No. 09/910,198 filed on Jul. 20, 2001 and issued as U.S. Pat. No. 6,818,456 on Nov. 16, 2004.

BACKGROUND OF THE INVENTION

The present invention generally relates to solid phase immunoassay tests for providing sensitive detection of an analyte in a biological fluid sample and is more particularly directed to a colored contrast method therefore.

Lateral flow immunoassay tests in typical use today, generally include a porous component of nitrocellulose membrane, as the solid, with specific reagent applied onto specific zones therein.

An upstream zone usually includes a specific binding reagent for the analyte being tested, conjugated to a visible label such as a gold colloid or colored latex particle. The labeled reagent is formulated to facilitate its release from the membrane after the sample is applied to the test strip.

In typical competition assays, a sample containing analyte is introduced to a sample area of the test strip. Migration of the sample, caused by the capillary wicking within the porous membrane; re-suspends the labeled reagent from its stationary position on the strip. As the reagent mixture migrates along the strip it is brought into contact with the immobilized capture reagent. If the analyte is present in the sample, binding to the labeled reagent (antibody-visual label) will take place during this migration.

If the amount of analyte is enough to exhaust all binding sites on the labeled reagent, binding of the visual label to the capture reagent will not occur. This constitutes a positive result.

If there is no analyte in the sample, the visual label will bind at the capture zone producing a negative result seen as a colored band or site.

For the most part, these tests are interpreted visually by human eye to determine the presence or absence of an analyte (drug). Membranes like nitrocellulose provide a white background to visualize the presence or absence of the colored line or site. Presently, white is the only color commercially available for nitrocellulose membrane.

Partial sight, aging, and congenital color deficits can produce changes in perception that reduce the visual effectiveness or certain color combinations.

The present invention provides for a method for enhancing visual perception of a colored site in lateral flow immunoassay device utilizing complementary colors to provide better contrast for visual perception of test results.

SUMMARY OF THE INVENTION

A method in accordance with the present invention for enhancing visual perception of a colored site in an immunoassay device includes dying the strip a color which is complimentary to the colored site produced by binding of the labeled reagent and the capture reagent or the step of providing a transparent film having a color which is complimentary to the colored site.

DETAILED DESCRIPTION

Figure 1:
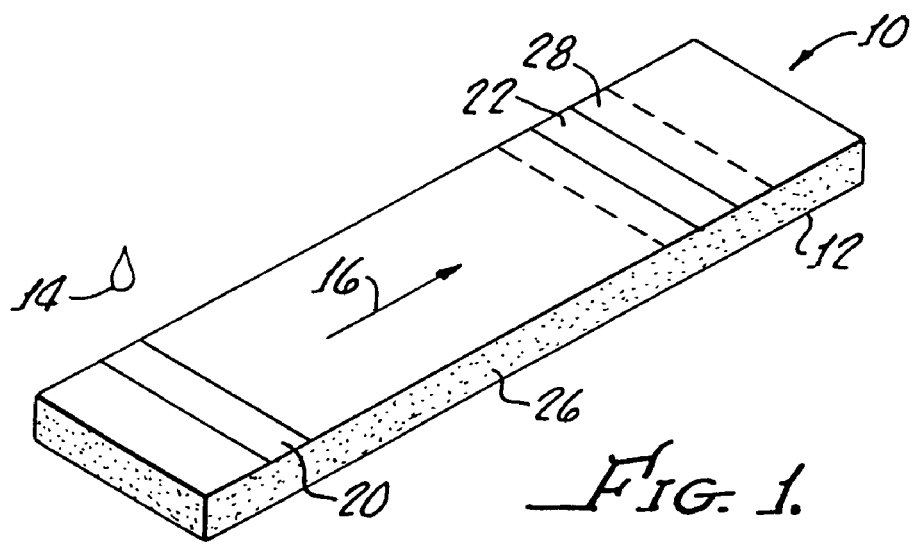
FIG. 1 is a perspective view of a lateral immunoassay generally showing a porous strip, a label reagent disposed on the strip along with a captive reagent immobilized on the strip and a representation of dye present in the strip for providing a color background.

With reference to FIG. 1, there is shown a lateral flow immunoassay device 10 which generally includes a porous strip 12, which typically is a nitrocellulose membrane or the like, which enables capillary migration of a fluid sample 14 therealong as represented by the arrow 16 after the deposition of the sample 14 onto the strip 12. The deposition preferably occurs on an area 20 of the strip where a labeled reagent is disposed. The labeled reagent is formulated, as is well known in the art, for suspension in the sample migrating therepast. A captive reagent is immobilized on the strip at a second zone 22 and formulated to bind to the labeled reagent to form a visible site on the strip.

In the embodiment 10 shown in FIG. 1, a dye 26, which is preferably indelible, is incorporated as an element which acts as a means for providing a complimentary color background for the colored site in order to increase visual perception of the colored site. Complimentary colors are those which appear generally opposite one another on a conventional color wheel which include the primary colors of yellow, blue and red.

Typical labeled reagents, such as, blue latex microparticles conjugated to drug antibody, and captive reagents such as, immobilized drug conjugates, result in a blue site. Complimentary colors for blue are yellow and orange which are "warm" colors that can optically move the subject, for example, the blue colored site to the foreground.

As hereinabove noted color compliments are color opposites. They are opposite each other on the color wheel, for example, blue is opposite orange and yellow. These colors are in extreme contrast to each other while making each more intense, for example, a bright orange or yellow background will highlight and make blue more vibrant.

This is an advantage to the visual interpretation of a lateral flow test when the signal to be interpreted becomes faint to the eye due to the quantity of analyte. In competitive assays, low amounts of analyte, under the proposed cut-off of the test, will weaken the visual signal to the point of producing a false positive. The present invention provides for a color contrast method that makes the color signal easier to see. In typical "sandwich" assays in which a colored line indicates a positive sample, colored contrast method in accordance with the present invention helps prevent false negatives particularly in person with color vision defects.

While a permanent dye 26 may be utilized, it should be appreciated that chemical components may be added to the strip which in fact cause a color background to be developed at the same time as binding of the labeling reagent in the captive reagent to form the colored site. For example, an anti BSA captive zone 28 may be provided under the capture zone 22, and broader thereof, and yellow latex microparticles introduced that have immobilized BSA on the surface with the blue latex microparticulates. As the sample runs, the yellow microparticulates will stop at the BSA captive zone 28, making it yellow, and if a drug was not present the blue microparticulates will stop at the captive zone 22.

Figure 2:
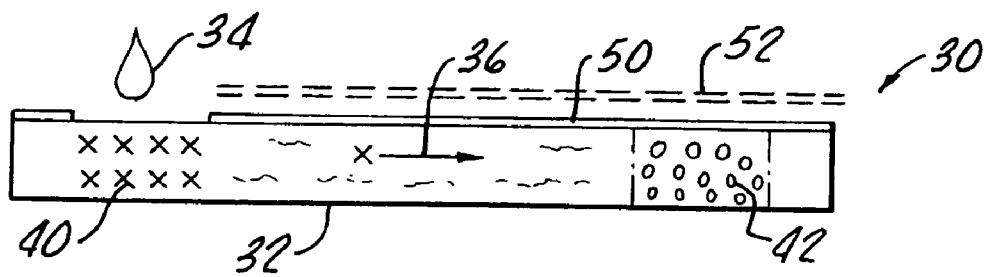
FIG. 2 is a cross-sectional view of a lateral immunoassay showing a porous strip immunoassay and representations of a labeled reagent disposed on the strip, a captive reagent immobilized on the strip and a transparent film for providing a complimentary background.

Alternatively, as shown in FIG. 2 a lateral flow immunoassay device 30, includes a porous strip 32 for enabling a sample to migrate therealong by capillary action as indicated by the arrow 36.

A labeled reagent 40 is disposed on the membrane and formulated as hereinabove noted for suspension in the sample 34 for migrating therepast. A captive reagent 42 is immobilized in the strip 32 in the path of sample migration and formulated to bind with the label reagent to form a visible colored site on the strip.

In the embodiment 30 the strip 32 may be a white porous membrane and a transparent film 50 of a selected color is disposed over the membrane strip 32. In order to provide a unitary device 30, the film 50 may be laminated to the membrane strip 32.

Alternatively, the film 50, which may be in the form of a plastic carrier or encasement 52, may be suspended above the strip 32 and include a transparent pigment for allowing light and the underlining test strip 32 to be visualized.

Figure 3:
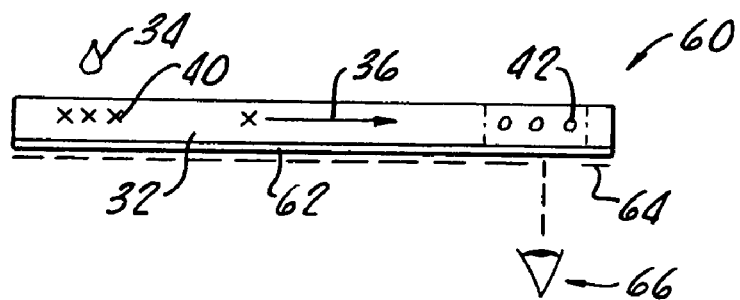
FIG. 3 is an alternative embodiment of the lateral immunoassay utilizing a nitrocellulose membrane on a colored backing.

An alternative immunoassay device 60 is shown in FIG. 3. Common references characters shown in FIG. 3 correspond to identical or similar reference characters shown in FIGS. 1 and 2.

The embodiment 60 includes the porous membrane 32 disposed on a transparent colored backing 62 preferably yellow Mylar®. Alternatively a clear Mylar® backing may be used with a transparent colored film 64, thereon as indicated in dashed line in FIG. 3. In this embodiment, the membrane 32 is viewed though the Mylar® (transparent colored backing) as indicated by the icon 66.

EXPERIMENTAL RESULTS

Lateral flow test strips were challenged with various levels of analytes and specimens. The levels were focused around the detection limits of the test device. The blue latex colored particles were used for the test. Two sets of identical test strips were challenged with the specimens. One set of the test strips where covered with a yellow Mylar® strip. Multiple individuals made visual reads of the strips and the readers commented on the ease of reading strips when the yellow film covered the test strip which enhanced their ability to interpret the presence or absence of the blue line result.

Although there has been hereinabove described a method for enhancing visual perception of colored site utilizing a specific complimentary colors of yellow and blue, it should be appreciated that the invention is not limited thereto but further incorporates the use of any sets of complimentary colors for enhancing visual equity of test results. Accordingly, any and all modifications, variations, or equivalent arrangements, which may occur to those skilled in the art should be considered to be within the scope of the invention as defined in the appended claims.

What is claimed is:

1. A method for improving detection sensitivity of a colored site in an immunoassay device, the device comprising a strip for enabling capillary migration of a fluid sample therealong, a labeled reagent disposed on the strip and formulated for suspension in the sample migrating therepast and a captive reagent immobilized on said strip in a path of sample migration and formulated to bind to said labeled reagent to form a visible colored site on the strip, the method comprising:
   providing a transparent film and disposing said film over said strip; and
   dyeing said transparent film to a color, which is complimentary to said colored site for providing enhanced observation of the visible colored site on said strip to improve detection sensitivity.

2. The method for improving detection sensitivity of the colored site in the immunoassay device of claim 1, wherein disposing the transparent film comprises suspending the transparent film above the strip.

3. The method for improving detection sensitivity of the colored site in the immunoassay device claim 1, wherein disposing the transparent film comprises laminating the transparent film to the strip.

4. The method for improving detection sensitivity of the colored site in the immunoassay device of claim 3, wherein the visible colored site is blue and wherein disposing the transparent film comprises disposing a transparent strip having a complimentary color selected from the group consisting of yellow, yellow-orange and orange.

5. The method for improving detection sensitivity of the colored site in the immunoassay device of claim 3, wherein the visible colored site is red and wherein disposing the transparent film comprises disposing a transparent strip having a complimentary color is selected from the group consisting of green, light green, fluorescent green and lime green.

* * * * *

UNITED STATES PATENT AND TRADEMARK OFFICE
CERTIFICATE OF CORRECTION

PATENT NO.         : 7,303,925 B2                                    Page 1 of 1
APPLICATION NO.    : 10/932399
DATED              : December 4, 2007
INVENTOR(S)        : Steven P. Sidwell and Steven S. Bachand It is certified that error appears in the above-identified patent and that said Letters Patent is hereby corrected as shown below:

On the Title page of the patent:

(12) Change "Sidewell" to -- Sidwell --.

(75) Inventors: Change "Sidewell" to -- Sidwell --.

Signed and Sealed this

Twenty-ninth Day of April, 2008

JON W. DUDAS
*Director of the United States Patent and Trademark Office*